United States Patent [19]

Zimmerhackl et al.

[11] Patent Number: 5,310,655
[45] Date of Patent: May 10, 1994

[54] PROCESS FOR THE DETECTION OF KIDNEY TUBULE FUNCTIONING

[75] Inventors: Lothar Zimmerhackl, Nimburg; Rolf Kinne, Dortmund; Thomas Fabricius, Dortmund; Fricke Pietruschka, Dortmund; Mathias Brandis, Freiburg, all of Fed. Rep. of Germany

[73] Assignee: Max-Planck-Gesellschaft zur Förderung der Wissenschaften E.V., Göttingen, Fed. Rep. of Germany

[21] Appl. No.: 663,832

[22] PCT Filed: Sep. 14, 1989

[86] PCT No.: PCT/EP89/01070

§ 371 Date: Mar. 22, 1991

§ 102(e) Date: Mar. 22, 1991

[87] PCT Pub. No.: WO90/03578

PCT Pub. Date: Apr. 5, 1990

[30] Foreign Application Priority Data

Sep. 23, 1988 [DE] Fed. Rep. of Germany ....... 3832432

[51] Int. Cl.$^5$ .............. C12Q 1/00; G01N 33/535; C12N 5/16
[52] U.S. Cl. ................. 435/7.9; 435/70.21; 435/240.27; 436/548; 530/388.26
[58] Field of Search ......... 530/388.26; 435/70.21, 435/240.27, 7.9; 436/503, 548

[56] References Cited

U.S. PATENT DOCUMENTS 4,575,486 3/1986 Laird .................... 435/29

OTHER PUBLICATIONS

Brunisholz et al.-Chem. Abst. vol. 104 (1986) p. 223,179.
Chemical Abstracts General Subject Index vols. 96-105 (1982-1986) pp. 28801GS-28802GS.
Characterization of monoclonal antibodies specific for human Tamm-Horsfall protein, M. Brunisholz, et al., Kidney International, vol. 29 (1986), pp. 971-976.
Pennica, D., et al. Science 236:83-88 (1987).

*Primary Examiner*—Sam Rosen
*Attorney, Agent, or Firm*—Felfe & Lynch

[57] ABSTRACT

In the case of a process for the detection of the functionability of the kidney tubules, one specifically determines the content of THP in the urine as measure of the function of the kidney tubules. One uses this process for the control of the transplant rejection after a kidney transplantation, for the detection of blood supply disturbances of the kidney and of kidney damages produced by prior oxygen deficiency supply. Processes for determining kidney function by measuring Tamm-Horsfall protein (THP) using a specific monoclonal antibody are disclosed.

9 Claims, No Drawings

PROCESS FOR THE DETECTION OF KIDNEY TUBULE FUNCTIONING

The invention concerns a process for the detection of the functioning of the kidney tubules and an antibody suitable therefor.

The kidney is one of the most important organs of the human organism. It serves to excrete from the blood the substances which the body no longer requires and to maintain the dynamic equilibrium of water and salt within the organism by means of osmotic regulation, excretion of water and water resorption. The morphological and functional units in which the formation of urine takes place are designated as nephrons. A nephron consists of the renal corpuscules in which the primary urine is filtered off and the tubule apparatus in which the urine concentration takes place. The renal corpuscule, which is also referred to as the glomerulus, is followed by the proximal tubule with its convoluted part, designated as the pars convoluta, and thereafter its straight part, designated as the pars recta, the epithelium of which is covered with a so-called hair-border membrane. There follows the transfer part which passes over into the thick ascending limb of the distal tubule. The transfer part and the ascending thick limb are combined under the designation loop of Henle. The distal tubule opens via its convoluted part into the collection tube which leads off the urine to the papilla tip and from there into the renal pelvis.

In the ascending limb of the loop of Henle a protein is formed which designated after its discoverers as Tamm-Horsfall protein (THP). The function and mode of action of this protein could hitherto not be conclusively elucidated.

Since the kidney is a very important organ, it is very important for clinical diagnosis to ascertain early damage of the kidney, as well as an impairment of its function. Admittedly, infectious diseases of the kidney can thereby be detected relatively simply by detection of the corresponding pathogens in the urine. Some other diseases of the kidney can also be diagnosed by detection of blood, amino acids or sugar in the urine. However, a decompensation of the kidney function does not, as a rule, make itself noticeable in the early stage by typical symptoms so that a diagnosis is difficult here. Just as as there was little possibility of monitoring the regeneration of cells of a transplanted kidney after a kidney transplant and to make statements regarding an acceptance or rejection. The sure coordination of these regeneration processes was hitherto only possible morphologically in biopsy material. Therefore, for the clinical diagnosis, it was very important to find a parameter in order to be able to ascertain organic disturbances of the kidney function early and without expenditure.

All experiments previously carried out to find a parameter which could be usable diagnostically for the control of the kidney function had the object of detecting damage of cells by detection of proteins which are excreted in the case of cell damage. An example herefor is the detection of villin in the urine. However, as a rule, these detection processes indicate very little since the appearance of these proteins in the urine can be attributed to the most varied causes and a direct correlation with particular function disturbances is not provided.

There are numerous publications about the role of THP in kidney diseases, as well as about how far the THP content in the urine could be evaluated diagnostically. The statements in the literature in this regard are contradictory. Some authors found that, in the case of certain diseases of the kidney, the THP content is increased, whereas other investigators found that the THP content is not influenced at all by diseases of the kidney. The contradictory results may thereby be due to non-specific methods of detection.

Therefore, it was the task of the invention to find a parameter which permits the control of the kidney function and to provide a process for the monitoring of the kidney function, as well as for the control of transplant rejections, which is simple to carry out and provides a dependable parameter. In particular, it was the task of the invention to find a parameter which indicates in good time a rejection crisis after a kidney transplant.

This task is solved by a process for the detection of the functionability of the renal tubules which is characterised in that one specifically determines the content of THP in the urine.

Surprisingly, it was found that the concentration of THP in the urine stands in good correlation with the state of health of the ascending limb of the loop of Henle. This region of the distal tubule reacts very sensitively to irregularities, especially to the insufficient supply of oxygen. Therefore, damages of the distal tubule are an indication for blood supply disturbances or of oxygen deficiency of the kidney, whereas, on the other hand, the normal function of the distal tubule indicates that damaged cells have regenerated. Therefore, a monitoring of the THP value permits the making of statements regarding the state of the kidney, especially regarding the organic functionability. Furthermore, the monitoring of the THP content in the urine is suitable to control the taking root of a kidney transplant and to recognise in good time a rejection crisis.

In healthy humans, the rate of excretion of THP is relatively constant and amounts to about 50 mg. per day. Therefore, if one compares the value obtained for a patient with this normal value, it can thus be estimated whether the kidney tubules have their complete function or are wholly or partly incapable of function.

The THP content of the urine is then only a dependable parameter when the THP is specifically detected without disturbance by other proteins present in the urine. Processes with which substances can be specifically detected, especially immunological processes, are known to the expert.

For the determination of THP, one preferably uses antibodies which bind specifically with the protein component of THP. Hitherto, for the detection of THP, antisera, i.e. polyclonal antibodies or monoclonal antibodies, were used, the specificity of which is unknown and of which only a part was specifically bindable with the protein component of the THP, whereas another part entered into a specific binding with the sugar component of the glycoprotein THP. However, with these known antisera, it results in cross-reactions with other glycoproteins or decomposition products of glycoproteins present in the urine. Therefore, in a preferred embodimental form of the process according to the invention, for the detection of THP in the urine, at least one antibody is used which binds specifically with the protein component of THP. For this purpose, a monoclonal antibody is preferably used.

Preferably, the detection of the THP in the urine takes place in per se known manner according to the principle of the immunoassay. In a preferred embodimental form, the detection of THP takes place by incubation with two receptors, one of which is bound to a solid phase or is immobilizable and the other carries a labelling, whereby one of the two receptors is an antibody or its fragment specifically binding with the protein component of THP. The other receptor can also be an antibody binding specifically with the protein component of THP. However, the second receptor can also be a receptor binding nonspecifically with THP or the complex of first receptor and THP-binding receptor. The binding of the one receptor to the solid phase or on a substance making possible an immobilization takes place in per se known manner and here requires no detailed explanation. The labelling of the other receptor can be radio-active, chemiluminescing, fluorescing or also an enzyme. For this purpose, too, processes are known to the expert, as well as for the evaluation of the labelling. In the case of the process according to the invention, there is especially preferably used a receptor which, as labelling, carries an enzyme or a fluorescing substance.

In an especially preferred embodimental form, THP is detected according to the principle of the immunoassay and, as specific antibody, there is used the monoclonal antibody produced by the cell line 2B3, deposited at the ECACC under the number 88092301 (in the following called monoclonal antibody 2B3). This antibody displays a very strong specificity for the protein component of THP and enters into practically no cross-reaction with other proteins and glycoproteins. With this antibody, THP can still be clearly detected to a concentration of 0.5 $\mu$g./ml. The values obtained are readily reproducable. The cell line 2B3 is also a subject of the invention.

A further subject of the invention is the use of the process according to the invention for the control of the transplant rejection after a kidney transplant. This takes place by individual or repeated investigations and makes possible a prognostic statement regarding the possibility of recovery and take up of function by the transplanted kidney. The process according to the invention permits the course of the growth of a transplanted kidney to be monitored. After the kidney transplantation, the tubule cells begin to regenerate. The further the regeneration process proceeds, the more these cells produce THP and thus the more THP can be detected in the urine. If, after the kidney transplantation, a decrease of the THP value occurs, then this indicates the commencement of a rejection crisis. Only when the normal value for the THP concentration is reached can one assume that the cells of the transplanted kidney work sufficiently.

The subject of the invention is also the use of the process according to the invention for the detection of blood supply disturbances of the kidney. This also takes place by individual or repeated investigations and there are also made possible prognostic statements regarding a normalization of the function. A decrease of the determined THP values indicates an insufficient supply of the distal tubule cells, which can be an indicator for blood supply disturbances in the kidney or for kidney damages produced by prior oxygen deficiency supply.

The invention is explained by the following Examples.

EXAMPLE 1

A calibration curve for the determination of THP according to the principle of the enzyme immunoassay was produced. For this purpose, the monoclonal antibody 2B3 was bound to the surface of microchamber plates. 100 $\mu$l. of sample solution were, in each case, incubated for one hour at room temperature with 100 $\mu$l. of peroxidase-coupled anti-human THP antibodies. After addition of 100 $\mu$l. of a solution which contained 0.1M citrate buffer, pH 4.5, 10 $\mu$l. H 0 and 10 mg. o-phenylenediamine, the extinction was measured at 492 nm after 30 minutes reaction. Solutions of THP with increasing THP content were used as sample solution.

EXAMPLE 2

Over a comparatively long period of time, the THP content was detected in the urine of children to whom a kidney had been transplanted. For this purpose, in each case, the excretion per 24 hours, the creatine concentration, as well as the THP concentration was determined. Since the daily creatine excretion in the urine is relatively constant, the creatine value serves as a standard value for the urine concentration and the ratio of THP concentration to creatine concentration gives a concentration-dependent excretion value for THP.

The results are to be seen from the following Table.

TABLE 1

| Days after kidney transplantation | 1 | 5 to 15 | 16 to 22 |
| --- | --- | --- | --- |
| $U_{THP}$ (mg./l.) | 1.63 | 24.75 | 55.13 |
| $A_{THP}$ (mg./d./1.73 m$^2$)* | 2.03 | 89.11 | 269.70 |
| $U_{THP}/U_{crea.}$ (mg./mmol) | 0.31 | 11.33 | 31.18 |

*The THP value obtained was here placed in relationship to the surface of the kidney tubules.

As is to be seen from this Table, the THP excretion was very low on the first day and then increased continuously. The value obtained for the 16th to 22nd day lies in the normal range. This shows that the distal tubule function of the transplanted kidneys had again reached the general functionability.

The preparation of monoclonal antibody 2B3 was accomplished by in vitro immunization of mouse spleen cells with purified THF protein from rabbits. Spleen cells from 2 Balb c mice (1.9×10$^8$ Z) were cultivated in 20 ml DMEM+20% fetal calf serum with 10 $\mu$g immunogen (purified Tamm-Horsfall protein (THF protein) from rabbit urine) for a period of 4 days. (Barbara D. Boss, Brain Research 291 (1984) 193-196).

After a culturing period of 4 days, the spleen cells were fused with 2×10$^7$ myeloma cells of the cell line SP2/O-Ag 14 and the hybridoma cells were selected in HAT medium. The antibodies produced were tested against the Tamm-Horsfall protein which was bound to microtiter plates and positive hybridoma cells were cloned. In the frozen section of the rabbit kidney, monoclonal antibody 2B3 binds on the apical cell membrane of the cells of the ascending branch of Henle's loop.

The 2B3 Hybridoma is on deposit as ECACC No. 88092301 at the European Collection of Animal Cell Cultures, PHLS Centre for Applied Microbiology and Research, Porton Down, Salisbury SP40JG, Wiltshire England.

It will be understood that the specification and examples are illustrative but not limitative of the present invention and that other embodiments within the spirit and scope of the invention will suggest themselves to those skilled in the art.

We claim:

1. A process for the detection of the level of functioning kidney tubules for a transplanted kidney function, a blood supply disturbance or kidney damage in a patient comprising determining the content of THP in a urine sample of said patient by immunoassay wherein a monoclonal antibody 2B3 (ECACC No. 88092301) reacts specifically with the protein component of urinary THP, by incubating the sample solution with the monoclonal antibody 2B3 and a labelled polyclonal specifically bindable with urinary THP or the complex of THP and the monoclonal antibody 2B3, and measuring the amount of the label as a measure of the amount of urinary THP to determine transplanted kidney function, extent of blood supply disturbance or extent of kidney damage.

2. Process according to claim 1, comprising using the monoclonal antibody 2B3 bound to a solid phase or in an immobilizable form.

3. Process according to claim 1, comprising using an enzyme or a fluorescence dyestuff as a label.

4. The method of claim 1 comprising determining the creatine concentration and determine the ratio of THP to creatine to give a concentration-dependent excretion value of THP.

5. The method of claim 1 comprising measuring the THP value in relationship to the surface area of the kidney tubules.

6. A process for the detection of the level of functioning kidney tubules for transplanted kidney function, blood supply disturbance or kidney damage in a patient comprising determining the content of THP in a urine sample of said patient by immunoassay wherein a monoclonal antibody 2B3 (ECACC No. 88092301) reacts specifically with the protein component of urinary THP, by incubating the sample solution with the monoclonal antibody 2B3, wherein the 2B3 is bound to a solid phase or in an immobilizable form, and a labelled polyclonal antibody specifically bindable with urinary THP or the complex of THP and 2B3, separating the solid from the liquid phase and measuring the amount of label in one of the two phases as a measure of the amount of urinary THP to determine transplanted kidney function, extent of blood supply disturbance or extent of kidney damage.

7. The method of claim 1 or 6 comprising measuring the creatine concentration and determining the ratio of THP to creatine to give a concentration-dependent excretion value for THP.

8. Hybridoma cell line 2B3 (ECACC number 88092301).

9. A monoclonal antibody 2B3 as produced by the hybridoma cell line 2B3 (ECACC No. 88092301).

* * * * *